United States Patent [19]

Carenzi et al.

[11] Patent Number: 4,985,428
[45] Date of Patent: Jan. 15, 1991

[54] ISOXAZOLES WITH NOOTROPIC ACTIVITY

[75] Inventors: Angelo Carenzi, Busto Arsizio; Dario Chiarino, Monza; Davide Della Bella; Mauro Napoletano, both of Milan; Alberto Sala, Monza, all of Italy

[73] Assignee: Zambon Group S.p.A., Venice, Italy

[21] Appl. No.: 302,747

[22] PCT Filed: May 19, 1988

[86] PCT No.: PCT/EP88/00445
§ 371 Date: Mar. 20, 1989
§ 102(e) Date: Mar. 20, 1989

[87] PCT Pub. No.: WO88/09330
PCT Pub. Date: Dec. 1, 1988

[30] Foreign Application Priority Data

May 20, 1987 [IT] Italy ............................. 20589 A/87
May 20, 1987 [IT] Italy ............................. 20590 A/87

[51] Int. Cl.$^5$ ................... A61K 31/495; A61K 31/42; C07D 261/18; C07D 413/12
[52] U.S. Cl. ..................................... 514/252; 514/326; 514/378; 514/380; 544/367; 546/209; 548/243; 548/248
[58] Field of Search .................. 544/367; 546/209; 548/243, 248; 514/252, 326, 378, 380

[56] References Cited

U.S. PATENT DOCUMENTS 3,459,738 8/1969 Morren et al. ................... 540/531
4,833,140 5/1989 Weber et al. ................... 514/424

FOREIGN PATENT DOCUMENTS 2024 9/1963 France .

OTHER PUBLICATIONS

Branconnier et al., *Psychopharmacology Bulletin*, 19, p. 726.
Moos et al., *Medicinal Research Reviews*, 8, pp. 353–391 (1988).
Hano et al., *Chemical Abstracts*, vol. 72, No. 132705 (1970).
Zeeh et al., *Chemical Abstracts*, vol. 95, No. 62168 (1981).

*Primary Examiner*—Mukund J. Shah
*Assistant Examiner*—E. Beinhardt
*Attorney, Agent, or Firm*—Stevens, Davis, Miller & Mosher

[57] ABSTRACT

Nootropically active isoxazoles which are certain specified derivatives of N-(5-isoxazolecarbonyl)-4 aminobutyric acid.

7 Claims, No Drawings

ISOXAZOLES WITH NOOTROPIC ACTIVITY

The present invention relates to compounds with nootropic activity and, more particularly, it relates to derivatives of N-(5-isox-azolecarbonyl)-4-aminobutyric acid, the processes for their preparation, their therapeutic use and the pharmaceutical compositions containing them as active ingredient.

Piracetam, 2-pyrrolidinoneacetamide (Merck Index, X edition, page 1080, no. 7363) is a compound described in Belgian Pat. No. 667906 (Union Chimique Belge) as central stimulant.

For its action at cerebral level on glucose metabolism as well as, especially, in increasing acetylcholine release, Piracetam is considered the parent compound of nootropic drugs and it is used in therapy in the treatment of cerebral efficiency disorders, particularly in elderly patients.

Piracetam, even if it is used in therapy, shows a relative effectiveness.

In order to improve the therapeutic activity of the parent compound several different compounds have been prepared.

Among these we can mention, for example, the derivatives of 1-benzoyl-2-pyrrolidinone described in European Pat. No. 5143 (Hoffmann-La Roche) and, particularly, the derivative known as Aniracetam, 1-(4-methoxy-benzoyl)-2-pyrrolidinone (USAN and the USP Dictionary of Drug Names 1987, page 30).

It is worth noting, however, that, as far as we know, the compounds with nootropic activity developed up to now do not contain an isoxazole ring and furthermore most of them have a remarkable structural analogy with the parent compound Piracetam.

Besides, as can be seen also in Aniracetam, the pyrrolidinone ring remains present, as peculiar characteristic.

We have surprisingly found and they are the object of the present invention, compounds of formula

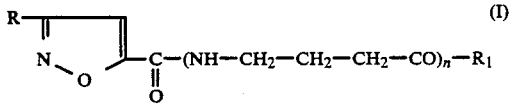 (I)

wherein n represents a number selected from 1 and 2;

R represents a hydrogen atom, a halogen atom, hydroxy, a $C_1$-$C_6$ alkyl or alkoxy;

$R_1$ represents hydroxy, an optionally unsaturated $C_1$-$C_{18}$ alkoxy or an

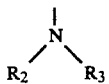

group;

$R_2$ and $R_3$, the same or different, represent a hydrogen atom, a linear or branched $C_1$-$C_6$ alkyl, a group of formula $(CH_2)_m R_4$ wherein m represents an integer selected from 1, 2 ,and 3;

$R_4$ represents a carboxy group, an alkoxycarbonyl group having from 1 to 6 carbon atoms in the alkoxy moiety or a group of formula

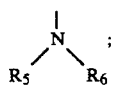

$R_5$ and $R_6$, the same or different, represent a hydrogen atom or a linear or branched $C_1$-$C_6$ alkyl;

or one of $R_2$ and $R_3$ represents a group of formula

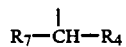

wherein $R_4$ has the above reported meanings and $R_7$ represents a linear or branched $C_1$-$C_4$ alkyl optionally substituted by phenyl, hydroxy or by a mercapto group; and the other represents a hydrogen atom;

or, in addition, $R_2$ and $R_3$, together with the nitrogen atom to which they are bonded, form a 5, 6 or 7 membered heterocycle which may further contain 1 or 2 heteroatoms selected among nitrogen, oxygen and sulphur.

Specific examples are 1-pyrrolidinyl, 1-piperazinyl, 4-methyl-1-piperazinyl, 1-piperidyl and 1-pyrrolidinyl-2-one.

A further object of the present invention are the salts of the compounds of formula I, which have an acidic function, with pharmaceutically acceptable organic or inorganic bases and the salts of the compounds of formula I, wherein $R_1$ contains a basic function, with organic or inorganic acids suitable for pharmaceutical use.

Examples of organic or inorganic bases useful as salifying agents are sodium or potassium hydroxides, ammonium hydroxide, lysine, arginine, cysteine and 2-amino-2-hydroxymethyl-1,3-propanediol. Examples of organic or inorganic acids useful as salifying agents are hydrochloric acid, hydrobromic acid, sulfuric acid, tartaric acid, citric acid and glutamic acid.

The compounds of formula I, object of the present invention, have nootropic activity.

Examples of compounds comprised in formula I are the following:

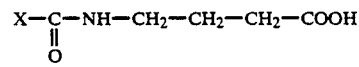

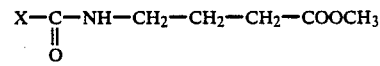

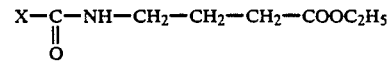

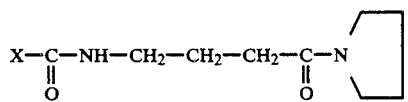
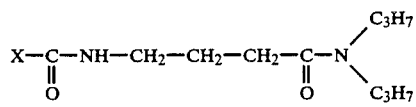
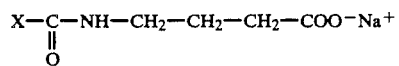
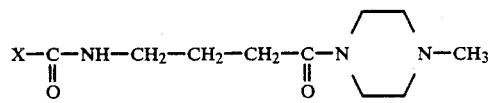
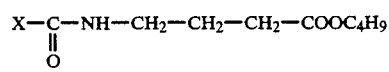
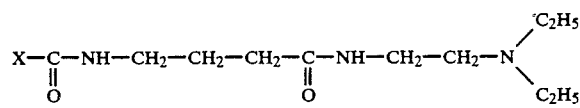
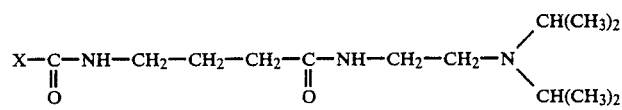
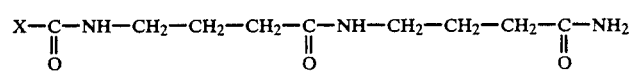
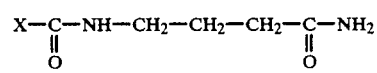
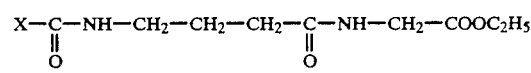
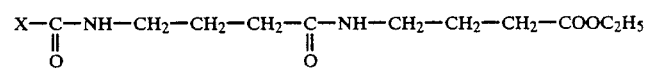
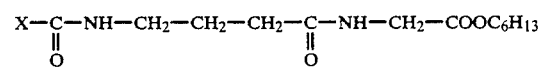
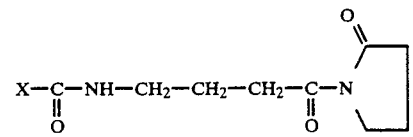
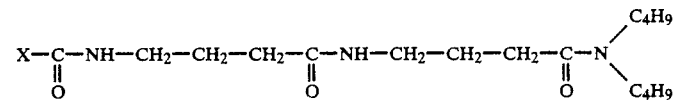
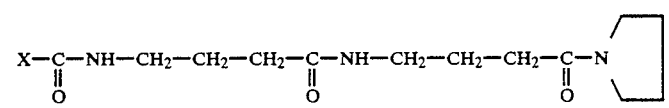
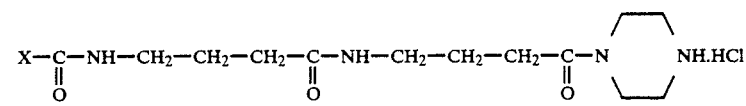

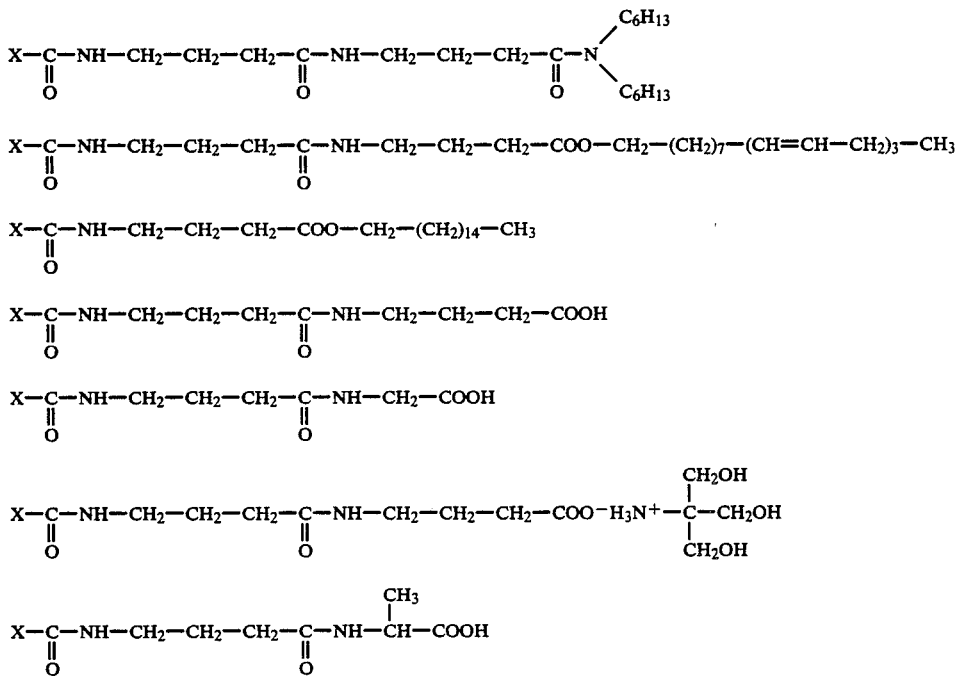

wherein
X represents the group of formula

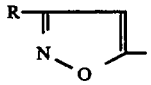

wherein R has the above reported meanings but preferably it represents a chlorine or bromine atom, hydroxy, methoxy or ethoxy, methyl or ethyl.

The preparation of the compounds of formula I is another object of the present invention and comprises a condensation reaction between a chloride of 5-isoxazolecarboxylic acid of formula

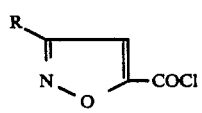  (II)

wherein
R has the above reported meanings, and 4-aminobutyric acid or a derivative thereof of formula <div style="text-align:center">H—(NH—CH$_2$—CH$_2$—CH$_2$—CO)$_n$—R$_1$      (II-A)</div> wherein
n and R$_1$ have the above reported meanings, in an inert solvent in the presence of an acceptor of halogenhydric acids.

Examples of suitable acceptors of halogenhydric acids are inorganic or organic bases such as sodium hydroxide or carbonate, triethylamine, N-methyl-morpholine and pyridine.

The reaction of compounds II with 4-aminobutyric acid (II-A n=1 R$_1$=OH) gives the compounds of formula I wherein n=1 and R$_1$=OH. Such compounds are transformed into their reactive derivatives such as mixed anhydrides and, without any isolation, they are condensed with 4-aminobutyric acid giving the compounds of formula I wherein n=2 and R$_1$=OH. For greater simplicity the compounds of formula I wherein R$_1$=OH will be indicated hereinafter as compound I-a)

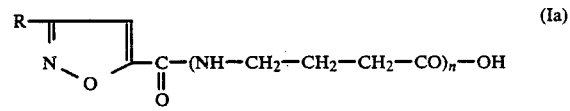  (Ia)

The compounds of formula I wherein R$_1$ is alkoxy are prepared from compounds Ia by esterification.

The esterification reaction is carried out with saturated or unsaturated aliphatic alcohols such as methanol, ethanol, propanol, butanol, cetylic alcohol, linolenic alcohol or stearic alcohol, in the presence of catalytic amounts of an inorganic acid.

The preparation of compounds I wherein

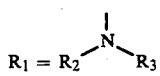

is carried out by reacting suitable reactive derivatives of compounds Ia with a suitable amino derivative according to the following reaction

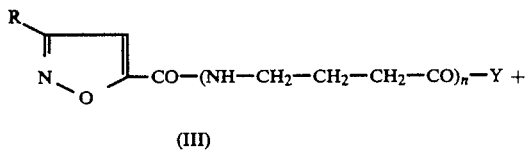

(III)

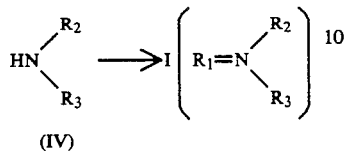

(IV)

wherein n, R, $R_1$, $R_2$ and $R_3$ have the above reported meanings and Y represents a leaving group.

Examples of reactive derivatives (III) of the compounds of formula Ia are mixed anhydrides obtainable by reaction with alkylchloroformates such as isobutylchloroformate.

Compounds III are, then, reacted, without any isolation, with an amino derivative of formula IV in a suitable solvent, which may be compound IV itself.

Examples of suitable amino derivatives of formula IV are ammonia, mono- or di-substituted amines such as methylamine, dimethylamine, diethylamine and di-n.propylamine; alkylendiamines such as N,N-diethyl-ethylendiamine and N,N-diisopropyl-ethylendiamine; cyclic derivatives such as pyrrolidine, 2-pyrrolidinone, piperazine and N-methyl-piperazine or natural aminoacids such as glycine, alanine, valine, serine, cysteine, phenylalanine and derivatives thereof.

The compounds of formula I wherein n=1 and the

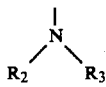

group is a 1-pyrrolidinyl-2-one may also be prepared from compounds Ia (n=2) by a cyclization reaction.

The cyclization reaction is carried out in one step through the formation of the corresponding acyl halide as intermediate. This intermediate, without any isolation, cyclizes in the same reaction environment giving the compound I wherein n=1 and

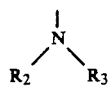

is a 1-pyrrolidinyl-2-one.

The intermediate acyl halides are prepared by reaction with a suitable halogenating agents such as thionyl chloride, phosphorus trichloride, phosphorus pentachloride, phosphorus tribromide, phosphorus pentachloride, oxalyl bromide and oxalyl chloride. For economical and practical reasons only, thionyl chloride is preferably used.

The cyclization reaction is carried out optionally in the presence of inert organic solvents such as toluene and benzene. It is clear to the man skilled in the art that the compounds of formula I, object of the present invention, can be prepared following alternative routes too.

For example the esterification of the carboxyl group can be carried out directly on 4-aminobutyric acid or a derivative thereof, that is before condensation with compound II.

In a similar way the compounds of formula I wherein

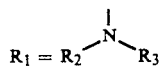

can be prepared also according to the following reaction

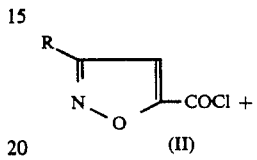

(II)

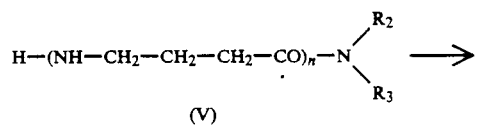

(V)

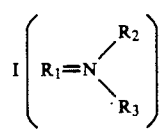

wherein n, R, $R_1$, $R_2$ and $R_3$ have the above reported meanings. According to this method, at first, the functionalization of the carboxyl group of 4-aminobutric acid or of 4-(4-aminobutyroyl)aminobutyric acid is carried out in order to obtain the amides of formula V.

These amides are, then, condensed with the acyl chloride of 5-isoxazolecarboxylic acid (II), in an inert organic solvent and in the presence of an acceptor of halogenhydric acids, to give the compounds of formula I wherein

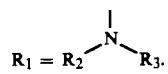

The compounds of formula I are active on central nervous system and they can be used in pharmaceutical field as nootropics. By the electroshock (ECS) amnesia test, described in example 8, in rat the pharmacological activity of the compounds object of the present invention was evaluated in comparison with the activity of Piracetam and Aniracetam.

The test results showed that the $ED_{50}$ values ($\mu$mol/kg) of the compounds of formula I are generally remarkably lower than that of Piracetam and Aniracetam.

Particularly, the $ED_{50}$ values are up to 20 times lower in case of "per os" administration and up to 10 times lower by perfusion than that of Piracetam.

The compounds of formula I have no toxicological problem. They exhibit a complete tolerability even when they are administered by perfusion at dose of 2 g/kg.

The therapeutic uses of the compounds object of the present invention are in the treatment of impairments of cerebral functionality due to ageing as well as to pathologic or traumatic reasons such as for example amnesia and decrease in cognitive capacity.

The therapeutic dose of the compounds of formula I and of the salts thereof depends on several factors such as the way of administration, the specific pharmaceutical composition, the treatment needed and the individual response to the therapy. In general it will be comprised between 5 and 2000 mg/day in one or more administrations.

A further object of the present invention are the pharmaceutical compositions containing the compounds of formula I or pharmaceutically acceptable salts thereof as active ingredient optionally together with one or more, solid or liquid, organic or inorganic pharmaceutical excipients such as diluents, preserving agents, moistening agents, colouring agents, flavouring agents and so on. The pharmaceutical compositions object of the present invention can be administered in solid pharmaceutical preparations, such as tablets, coated tablets, capsules, granulates and suppositories or in liquid pharmaceutical preparations such as syrups, suspensions, emulsions and solutions suitable for oral or parenteral administration.

The compounds object of the present invention can be prepared in slow and protracted release pharmaceutical formulations too. The pharmaceutical compositions object of the present invention may also contain the compounds of formula I or pharmaceutically acceptable salts thereof in association with other active ingredients selected, for example, among aminoacids, N-acetyl-cysteine, co-enzymes, mineral salts and vitamins.

The preparation of the pharmaceutical compositions object of the present invention is carried out by usual techniques.

In order to better illustrate the present invention, the following examples are now given.

EXAMPLE 1

Preparation of
N-(3-bromo-5-isoxazolecarbonyl)-4-aminobutyric acid
(Compound no. 1)

To a solution of 4-aminobutyric acid (11.34 g; 0.11 mol) and sodium hydroxide (4.4 g; 0.11 mol) in water (150 ml), cooled at 10° C., a solution of 3-bromo-5-isoxazolecarbonylchloride (21 g; 0.10 mol) in toluene (150 ml) and a solution of sodium hydroxide (4.0 g; 0.10 mol) in water (150 ml) were added simultaneously. The reaction mixture was kept under stirring at room temperature for 2 hours. The aqueous layer was separated, washed with toluene (150 ml) and acidified with concentrated hydrochloric acid up to pH 2.

The precipitate was extracted three times with ethyl acetate (200 ml). The organic extracts were collected, washed with water and dried on sodium sulphate.

After evaporation of the solvent, the solid crude was cristallized from acetonitrile (150 ml) giving N-(3-bromo-5-isoxazolecarbonyl)-4-aminobutyric acid (23 g; 83% yield) with m.p. 140°-141° C. $^1$H-NMR (DMSO-$d_6$): delta (ppm): 1.6-2.1 (2H, m, $CH_2$—$CH_2$—$CH_2$); 2.1-2.5 (2H, m, $CH_2CO$); 3.33 (2H, q, $CH_2\overline{N}$); 7.39 (1H, s, —CH=).

In a similar way the following compounds were prepared.

N-(3-chloro-5-isoxazolecarbonyl)-4-aminobutyric acid (Compound no. 2)

m.p. 140°-141° C. (acetonitrile); 81% yield.
$^1$H-NMR (DMSO-$d_6$): delta (ppm): 1.5-2.1 (2H, m, $CH_2$—$CH_2$—$CH_2$); 2.1-2.6 (2H, m, $CH_2CO$); 3.36 (2H, q, $CH_2\overline{N}$); 7.39 (1H, s, —CH=).

N-(3-methoxy-5-isoxazolecarbonyl)-4-aminobutyric acid (Compound no. 3)

m.p. 134°-135° C. (acetonitrile); 78% yield.
$^1$H-NMR (DMSO-$d_6$): delta (ppm): 1.5-2.1 (2H, m, $CH_2$—$CH_2$—$CH_2$); 2.1-2.5 (2H, m, $CH_2CO$); 3.29 (2H, q, $CH_2\overline{N}$); 3.97 (3H, s, $CH_3O$); 6.82 (1H, s, —CH=).

N-(3-methyl-5-isoxazolecarbonyl)-4-aminobutyric acid (Compound no. 4)

m.p. 136°-137° C. (acetonitrile); 75% yield. $^1$H-NMR (DMSO-$d_6$): delta (ppm): 1.5-2.1 (2H, m, $CH_2$—$CH_2$—$CH_2$); 2.1-2.5 (2H, m, $CH_2CO$); 2.32 (3H, s, $C\overline{H}_3$); 3.29 (2H, q, $CH_2\overline{N}$); 7.00 (1H, s, —CH=).

N-(3-n.butyl-5-isoxazolecarbonyl)-4-aminobutyric acid (Compound no. 5)

m.p. 130°-131° C. (acetonitrile); 75% yield.
$^1$H-NMR (DMSO-$d_6$): delta (ppm): 0.90 (3H, t, $CH_3$); 1.32 (2H, m, $CH_2$—$CH_3$); 1.61 (2H, m, $CH_2$—$CH_2$—$CH_3$); 1.73 (2H, m, $CH_2$—$CH_2$—CO); 2.26 (2H, dd, $CH_2CO$); 2.66 (2H, dd, $CH_2$—C=); 3.25 (2H, m, N—$CH_2$); 6.96 (1H, s, —CH=); 8.92 (1H, s, NH); 12.12 (1H, s, OH).

N-(5-isoxazolecarbonyl)-4-aminobutyric acid (Compound no. 6) m.p. 149°-151° C. (acetonitrile); 64% yield.
$^1$H-NMR (DMSO-$d_6$): delta (ppm): 1.75 (2H, m, $CH_2$—$CH_2$—$CH_2$); 2.27 (2H, t, $CH_2CO$); 3.27 (2H, dt, N—$C\overline{H}_2$); 7.06 (1H, d, —CH=C); 8.74 (1H, d, —CH=N); 8.99 (1H, s, NH); 12.12 (1H, s, OH).

EXAMPLE 2

Preparation of ethyl
N-(3-bromo-5-isoxazolecarbonyl)-4-aminobutyrate
(Compound no. 7)

A suspension of N-(3-bromo-5-isoxazolecarbonyl)-4-aminobutyric acid (10 g; 0.036 mol), prepared according to the method described in example 1, in absolute ethanol (300 ml), containing a catalytic amount of concentrated $H_2SO_4$, was kept under stirring at room temperature for 24 hours.

The obtained solution was evaporated to dryness and the solid residue was dissolved in water (100 ml) and extracted 3 times with ethyl acetate (100 ml).

The organic extracts were collected, washed with water, dried on sodium sulphate and evaporated.

The solid residue was crystallized from diisopropyl ether (100 ml) obtaining ethyl N-(3-bromo-5-isoxazolecarbonyl)-4-aminobutyrate (9.1 g; 83% yield) with m.p. 72°-3° C.

$^1$H-NMR (DMSO-$d_6$): delta (ppm): 1.18 (3H, t, $CH_3$); 1.5-2.2 (2H, m, $CH_2$—$CH_2$—$CH_2$); 2.2-2.6 (2H, m, $CH_2CO$); 3.32 (2H, q, $C\overline{H}_2N$); 4.08 (2H, q, $\underline{C}H_2$—$CH_3$); 7.40 (1H, s, —CH=).

EXAMPLE 3

N-[4-oxo-4-(1-pyrrolidinyl)butyl]-3-bromo-5-isoxazolecarboxamide (Compound no. 8)

To a solution of N-(3-bromo-5-isoxazolecarbonyl)-4-aminobutyric acid (11.8 g; 0.04 mol), prepared according to the method described in example 1, and N-methyl-morpholine (4.41 ml; 0.04 mol) in anhydrous tetrahydrofuran (260 ml), cooled at −15° C., isobutylchloroformate (5.22 ml; 0.04 mol) was slowly added.

After standing under stirring at −10° C. for 15 minutes, a solution of pyrrolidine (3.30 ml; 0.04 mol) in anhydrous tetrahydrofuran (10 ml) was added dropwise to the reaction mixture kept at the same temperature.

At the end of the addition it was kept under stirring for 12 hours at room temperature.

After evaporation of the solvent, the residue was dissolved in chloroform (150 ml). The solution was washed with HCl 0.1N (50 ml), with water, with an aqueous solution of $K_2CO_3$ and finally several times with water up to neutral pH.

The organic layer was dried on sodium sulphate and, after evaporation of the solvent, the solid residue was crystallized from ethyl acetate (100 ml) obtaining N-[4-oxo-4-(1-pyrrolidinyl)butyl]-3-bromo-5-isoxazolecarboxamide (10.9 g; 82% yield) with m.p. 120°-121° C.

$^1$H-NMR (DMSO-$d_6$): delta (ppm): 1.5-2.1 [6H, m, $CH_2$—$CH_2$—$CH_2$, $CH_2$—$(CH_2)_2$—$CH_2$]; 2.1-2.5 (2H, m, $CH_2CO$); 3.1-3.7 (6H, m, $CH_2N$, $CH_2$—N—$CH_2$); 7.46 (1H, s, —CH=).

In a similar way the following compounds were prepared:

N-[4-(4-methyl-1-piperazinyl)-4-oxobutyl]-3-bromo-5-isoxazolecarboxamide (Compound no. 9)

m.p. 124°-125° C. (ethyl acetate); 85% yield.

$^1$H-NMR (DMSO-$d_6$): delta (ppm): 1.5-2.0 (2H, m, $CH_2$—$CH_2$—$CH_2$); 2.0-2.5 (9H, m, $CH_2CO$,

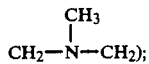

3.1-3.7(6H, m, $CH_2N$,

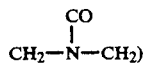

7.36 (1H, s, —CH=).

N-[4-[2-(diethylamino)ethylamino]-4-oxobutyl]-3-bromo-5-isoxazolecarboxamide (Compound no. 10)

m.p. 80°-82° C. (ethyl acetate); 65% yield.

$^1$H-NMR (DMSO-$d_6$): delta (ppm): 0.93 (6H, t, $2CH_3$); 1.5-2.8 [10H, m, $(CH_2)_2CO$, $CH_2$—N—$(CH_2$—$CH_3)_2$]; 2.9-3.5 (4H, m, $2CH_2N$); 7.37 (1H, s, —CH=).

N-[4-[2-(diisopropylamino)ethylamino]-4-oxobutyl]-3-bromo-5-isoxazolecarboxamide (Compound no. 11)

m.p. 81°-83° C. (diisopropyl ether-ethyl acetate); 78% yield.

$^1$H-NMR (DMSO-$d_6$): delta (ppm): 0.96 (12H, d, $4CH_3$); 1.5-3.6 (12H, m, $5CH_2$, 2CH); 7.41 (1H, s, —CH=).

Ethyl N-[N-(3-bromo-5-isoxazolecarbonyl)-4-aminobutyroyl]glicinate (Compound no. 12)

m.p. 72°-73° C. (diisopropyl ether); 88% yield.

$^1$H-NMR (DMSO-$d_6$): delta (ppm): 1.19 (3H, t, $CH_3$); 1.5-2.1 (2H, m, $CH_2$—$CH_2$—$CH_2$); 2.1-2.4 (2H, m, $CH_2CO$); 3.33 (2H, q, $CH_2$—$CH_2$—N); 3.87 (2H, d, N—$CH_2$—CO); 4.16 (2H, q, $CH_2$—$CH_3$); 7.46 (1H, s, —CH=).

Ethyl N-[N-(3-bromo-5-isoxazolecarbonyl)-4-aminobutyroyl]-4-aminobutyrate (Compound No. 13)

m.p. 121°-122° C. (ethyl acetate); 89% yield.

$^1$H-NMR (DMSO-$d_6$): delta (ppm): 1.18 (3H, t, $CH_3$); 1.5-2.6 (8H, m, $2CH_2$—$CH_2CO$); 2.8-3.6 (4H, m, $2CH_2N$); 4.09 (2H, q, $CH_2CH_3$); 7.39 (1H, s, —CH=).

4-[N-(3-bromo-5-isoxazolecarbonyl)-amino]-butyramide (Compound no. 14)

m.p. 178°-179° C. (ethanol); 61% yield $^1$H-NMR (DMSO-$d_6$): delta (ppm): 1.72 (2H, m, $CH_2$—$CH_2$—$CH_2$); 2.09 (2H, dd, $CH_2CO$); 3.24 (2H, m, N—$CH_2$); 6.78 (1H, s, H—N—H); 7.29 (1H, s, H—N—H); 7.34 (1H, s, —CH=); 9.06 (1H, t, NH—$CH_2$).

4-[[N-(3-bromo-5-isoxazolecarbonyl)-4-aminobutyroyl]-amino]-butyramide (Compound no. 15)

m.p. 202°-204° C. (dimethylformamide); 72% yield.

$^1$H-NMR (DMSO-$d_6$): delta (ppm): 1.58-1.73 (4H, m, $2CH_2$—$CH_2$—$CH_2$); 2.03 (2H, dd, $CH_2CONH_2$); 2.10 (2H, dd, $CH_2$—CONH); 3.01-3.23 (4H, m, $2NHCH_2$); 6.73 (1H, s, H—N—H); 7.25 (1H, s, H—N—H); 7.34 (1H, s, —CH=); 7.82-9.06 (2H, s, 2CONH).

n.hexyl N-(3-bromo-5-isoxazolecarbonyl)-4-aminobutyrate (Compound no. 16)

m.p. 52°-54° C. (hexane); 44% yield.

$^1$H-NMR (DMSO-$d_6$): delta (ppm): 0.86 (3H, t, $CH_3$); 1.2-1.3 [6H, m, $(CH_2)_3CH_3$]; 1.5-1.6 (2H, m, OCH$_2$—$CH_2$); 1.77 (2H, m, $CH_2$—$CH_2$—CO); 2.36 (2H, t, $CH_2CO$); 3.28 (2H, m, N—$CH_2$); 3.99 (2H, t, OCH$_2$); 7.35 (1H, s, —CH=); 9.07 (1H, t, NH).

1-[N-[N-(3-bromo-5-isoxazolecarbonyl)-4-aminobutyroyl]-4-aminobutyroyl]pyrrolidine (Compound no. 17)

m.p. 157°-159° C. (dimethylformamide); 53% yield.

$^1$H-NMR (DMSO-$d_6$): delta (ppm): 1.5-1.9 (8H, m, $4CH_2$); 2.10 (2H, dd, $CH_2CO$); 2.21 (2H, dd, $CH_2CO$); 3.04 (2H, m, NHCH$_2$); 3.2-3.4 (6H, m, $3CH_2N$); 7.35 (1H, s, —CH=); 7.83 (1H, t, CONH); 9.06 (1H, t, CONH).

EXAMPLE 4

Preparation of N-[4-(di-n.propylamino)-4-oxobutyl]-3-bromo-5-isoxazolecarboxamide (Compound no. 18)

A solution of 3-bromo-5-isoxazolecarbonyl chloride (2.95 g; 0.014 mol) in methylene chloride (5 ml) was added dropwise to a solution, cooled at 5° C., of 4-aminobutyric acid di-n.propylamide (2.60 g; 0.014 mol) and triethylamine (1.95 ml; 0.014 mol) in methylene chloride (52 ml).

At the end of the addition the reaction mixture was kept under stirring for 6 hours at room temperature and then it was extracted with HCl 0.1N (20 ml), with water, with a saturated aqueous solution of NaHCO$_3$ (20 ml) and finally with water up to neutral pH.

The organic layer was dried on sodium sulphate and, after evaporation of the solvent, the solid residue was crystallized from diisopropylether.

N-[4-(di-n.propylamino)-4-oxobutyl]-3-bromo-5-isoxazolecarboxamide (3.6 g; 71% yield) was obtained with m.p. 78°-79° C.

$^1$H-NMR (DMSO-$d_6$): delta (ppm): 0.82 (6H, t, $2CH_3$); 1.1-2.1 (6H, m, $2CH_2CH_3$, $CH_2$—$CH_2$—$CH_2$); 2.1-2.5 (2H, m, $CH_2CO$); 3.0-3.5 (6H, m, $CH_2NH$, $2CH_2N$); 7.33 (1H, s, —CH=).

EXAMPLE 5

Preparation of N-[N-(3-bromo-5-isoxazolecarbonyl)-4-aminobutyroyl]-4-aminobutyric acid (Compound no. 19) Method A To a solution of ethyl N-[N-(3-bromo-5-isoxazolecarbonyl)-4-aminobutyroyl]-4-aminobutyrate (23.6 g; 0.061 mol), prepared according to the method described in example 3, in methanol (236 ml), cooled at 10° C., a solution of sodium hydroxide (2.64 g; 0.065 mol) in water (60 ml) was added dropwise.

At the end of the addition, it was kept under stirring at room temperature for 18 hours.

After evaporation of most solvent, the solution was diluted with water (200 ml) and extracted twice with chloroform (50 ml). The aqueous layer was acidified to pH 2 with HCl at 10%. The precipitate was filtered, washed with water up to neutral pH and it was crystallized from isopropanol (200 ml).

N-[N-(3-bromo-5-isoxazolecarbonyl)-4-aminobutyroyl]-4-aminobutyric acid was obtained (20.8 g; 94% yield) with m.p. 157°–158° C.

$^1$H-NMR (DMSO-$d_6$): delta (ppm): 1.4–2.5 (8H, m, 2CH$_2$—CH$_2$—CO); 2.8–3.6 (4H, m, 2CH$_2$N); 7.37 (1H, s, —CH=).

In a similar way the following compound was prepared.

N-[N-(3-bromo-5-isoxazolecarbonyl)-4-aminobutyroyl]glycine (Compound no. 20)

m.p. 187°–189° C. (isopropanol); 91% yield.

$^1$H-NMR (DMSO-$d_6$): delta (ppm): 1.5–2.0 (2H, m, CH$_2$—CH$_2$—CH$_2$); 2.0–2.5 (2H, m, CH$_2$—CH$_2$—CO); 3.0–3.6 (2H, m, CH$_2$—CH$_2$N); 3.80 (2H, d, CH$_2$COO); 7.43 (1H, s, —CH=).

Method B

To a solution of N-(3-bromo-5-isoxazolecarbonyl)-4-aminobutyric acid (69.27 g; 0.25 mol), prepared according to the method described in example 1, and triethylamine (34.80 ml; 0.25 mol) in anhydrous tetrahydrofuran (700 ml), cooled at −15° C., isobutylchloroformate (32.67 ml; 0.25 mol) was added slowly.

After stirring at −10° C. for 15 minutes, a solution of 4-aminobutyric acid (30.94 g; 0.30 mol) and triethylamine (41.76 ml; 0.30 mol) in water (190 ml) and dimethylformamide (60 ml) was added dropwise keeping the reaction mixture at the same temperature.

After stirring at room temperature for 3 hours, the solvent w evaporated and the residue was dissolved in water (350 ml). The obtained aqueous solution was acidified with HCl at 10% and the precipitate was filtered, washed with water up to neutral pH and it was crystallized from isopropanol (600 ml).

N-[N-(3-bromo-5-isoxazolecarbonyl)-4-aminobutyroyl]-4-aminobutyric acid was obtained (55.5 g; 61% yield) with m.p. 157°–158° C.

EXAMPLE 6

Preparation of 1-[N-(3-bromo-5-isoxazolecarbonyl)-4-aminobutyroyl]-2-pyrrolidinone (Compound no. 21)

A solution of 1-[N-(3-bromo-5-isoxazolecarbonyl)-4-aminobutyroyl]-4-aminobutyric acid (9.0 g; 0.0025 mol), prepared according to the method described in example 5, and thionyl chloride (2.72 ml; 0.0375 mol) in toluene (250 ml) was heated under reflux for 15 minutes.

After cooling and evaporation of the solvent, the solid residue was cristallized from absolute ethanol (60 ml) giving 1-[N-(3-bromo-5-isoxazolecarbonyl)-4-aminobutyroyl]-2-pyrrolidinone (7.6 g; 88% yield) with m.p. 141°–142° C.

$^1$H-NMR (DMSO-$d_6$): delta (ppm): 1.6–2.3 (4H, m, 2CH$_2$—CH$_2$—CH$_2$); 2.3–4.0 (8H, m, 2CH$_2$N, 2CH$_2$CO); 7.41 (1H, s, —CH=).

EXAMPLE 7

N-(3-bromo-5-isoxazolecarbonyl)-4-aminobutyric acid 2-amino-2-hydroxymethyl-1,3-propanediol salt (Compound no. 22)

To a solution of N-(3-bromo-5-isoxazolecarbonyl)-4-aminobutyric acid (11.08 g; 0.04 mol), prepared according to the method described in example 1, in aqueous ethanol at 95% (80 ml), 2-amino-2-hydroxymethyl-1,3-propanediol (4.85 g; 0.04 mol) was added and the solution was stirred for 30 minutes at room temperature. After evaporation of the solvent, the solid residue was crystallized from isopropanol (160 ml) giving N-(3-bromo-5-isoxazolecarbonyl)-4-aminobutyric acid 2-amino-2-hydroxymethyl-1,3-propanediol salt (14.8 g; 93% yield) with m.p. 133°–135° C.

$^1$H-NMR (DMSO-$d_6$): delta (ppm): 1.72 (2H, m, CH$_2$—CH$_2$—CH$_2$); 2.14 (2H, dd, CH$_2$CO); 3.25 (2H, m, N—CH$_2$); 3.37 (6H, s, 3CH$_2$O); 5.73 (6H, broad s, exchangeable protons); 7.35 (1H, s, —CH=); 9.39 (1H, t, CONH).

In a similar way the following compound was prepared.

N-(3-bromo-5-isoxazolecarbonyl)-4-aminobutyric acid sodium salt (Compound no. 23)

m.p. >200° C. (ethanol); 87% yield.

$^1$H-NMR (D$_2$O): delta (ppm): 1.78 (2H, m, CH$_2$—CH$_2$—CH$_2$); 2.18 (2H, dd, CH$_2$CO); 3.31 (2H, dd, N—CH$_2$); 7.03 (1H, s, —CH=).

EXAMPLE 8

Pharmacodynamic evaluation: electroshock (ECS) amnesia test in rat

Male rats weighing 130–150 g and fasting for at least 12 hours before the beginning of the test were used.

The test consisted in two experiments with a resting interval of 24 hours between them.

First experiment: training session

The animals were trained to associate the passage from a light partition to a dark one, in a suitable box, with a noxious stimulation that is an electric stimulation through an electrified grid (foot-shock: 1 mA for 10 seconds).

Second experiment: retention session

The ability of the animals to remember was evaluated as the time utilized to repeat the passage through the partitions (retention time).

Evaluation of the retention time in control groups of animals

The test was carried out first on two groups of animals as control.

A first group of rats (hereinafter indicated as control), which remembered the association between the passage and the noxious stimulation, showed a conditioned response that led to avoid the repetition of the passage.

A second group of animals (hereinafter indicated as ECS control), which underwent a treatment for inducing amnesia (ECS: 90 mA, 100 Hz for 1 second) immediately after the training session, showed a decreased conditioned response and a large number of rats repeated the passage.

Fixing 60 seconds as time-limit for performing the second experiment, the average time (retention time) utilized for the passage was 54 seconds for the control and 32 seconds for the ECS control.

Evaluation of the retention time in groups of treated animals

Groups of 20 rats underwent the training session, the treatment for inducing amnesia and the retention session after administration of the compounds object of the present invention and of the reference compounds, Piracetam and Aniracetam.

The administration was carried out 30 minutes before the training session in case of intraperitoneal administration (i.p.) and 60 minutes before in case of administration by oral route. At least three doses each compound and each administration route were tested.

The difference between the retention time of the control and the retention time of the ECS control was considered as reference ($\Delta t$) and it was fixed, as percentage, equal to 100.

In the groups of animals which were treated and underwent ECS the activity against amnesia of the compounds object of the present invention was expressed as $ED_{50}$ that is as the dose of compound able to give an improvement of the retention time equal to 50% of the reference interval ($\Delta t$) in comparison with the ECS control. As example the $ED_{50}$ values of some representatives of the compounds of formula I are reported in table 1.

TABLE 1

| Compound no. | $ED_{50}$ i.p. ($\mu$mol/kg) | $ED_{50}$ os ($\mu$mol/kg) |
| --- | --- | --- |
| 1 | 102 | 290 |
| 2 | 160 | 260 |
| 3 | 276 | 868 |
| 4 | 202 | 383 |
| 8 | 25 | 80 |
| 12 | 171 | 1000 |
| 19 | — | 261 |
| 21 | — | 254 |
| Piracetam | 329 | 1550 |
| Aniracetam | 353 | 1110 |

We claim:

1. A compound of formula

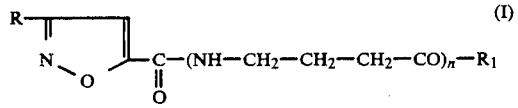

wherein n represents a number selected from 1 and 2;

R represents a hydrogen atom, a halogen atom, hydroxy, a $C_1$-$C_6$ alkyl or alkoxy;

$R_1$ represents hydroxy, an optionally unsaturated $C_1$-$C_{18}$ alkoxy or an

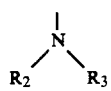

group;

$R_2$ and $R_3$, the same or different, represent a hydrogen atom, a linear or branched $C_1$-$C_6$ alkyl, or a group of formula $(CH_2)_m R_4$ wherein m represents an integer selected from 1, 2 and 3;

$R_4$ represents a carboxy group, an alkoxycarbonyl group having from 1 to 6 carbon atoms in the alkoxy moiety or a group of formula

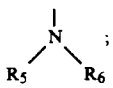

$R_5$ and $R_6$, the same or different, represent a hydrogen atom or a linear or branched $C_1$-$C_6$ alkyl;

or one of $R_2$ and $R_3$ represents a group of formula

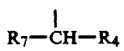

wherein $R_4$ has the above meanings and $R_7$ represents a linear or branched $C_1$-$C_4$ alkyl optionally substituted by phenyl, hydroxy or by a mercapto group, and the other one of $R_2$ and $R_3$ represents a hydrogen atom;

or in addition $R_2$ and $R_3$, together with the nitrogen atom to which they are bonded, form a heterocyclic selected among the class consisting of 1-pyrrolidinyl, 1-piperazinyl, 4-methyl-1-piperazinyl, 1-piperidyl and 1-pyrrolidinyl-2-one;

and pharmaceutically acceptable salts thereof.

2. A compound, according to claim 1, wherein R represents chlorine, bromine, hydroxy, methoxy, ethoxy, methyl or ethyl.

3. A compound, according to claim 1 or 2, wherein $R_1$ represents hydroxy.

4. A pharmaceutical composition with nootropic activity comprising a nootropically effective amount of a compound according to claim 1 or 2 together with one or more exipients suitable for pharmaceutical use.

5. A method for the treatment of impairments of cerebral functionality due to aging as well as to pathologic or traumatic reasons which are treatable comprising administering a nootropically effective amount of a compound according to claim 1 or 2.

6. A compound of claim 1 wherein $R_1$ is selected from the group consisting of $OCH_3$, $OC_2H_5$, $OC_4H_9$, $OC_6H_{13}$, $O-CH_2-(CH_2)_7-(CH=CH-CH_2)_3-CH_3$ or $-O-CH_2-(CH_2)_{14}-CH_3$).

7. A compound of claim 1 wherein $R_1$ is $N(R_2)(R_3)$ and $N(R_2)(R_3)$ is selected from the group consisting of pyrrolidine, 2-pyrrolidinone, piperazine, N-methyl-piperazine, glycine, alanine, valine, serine, cysteine and phenylalanine.

* * * * *